(12) United States Patent
Pierce et al.

(10) Patent No.: US 8,653,317 B2
(45) Date of Patent: Feb. 18, 2014

(54) DEHYDROGENATION PROCESS AND CATALYST

(75) Inventors: Richard A. Pierce, Lake Jackson, TX (US); Lin Luo, Lake Jackson, TX (US); Michael M. Olken, Midland, MI (US); Susan Domke, Rosharon, TX (US); Howard W. Clark, Lake Jackson, TX (US)

(73) Assignee: Dow Global Technologies LLC

( * ) Notice: Subject to any disclaimer, the term of this patent is extended or adjusted under 35 U.S.C. 154(b) by 415 days.

(21) Appl. No.: 12/717,453

(22) Filed: Mar. 4, 2010

(65) Prior Publication Data

US 2010/0236985 A1    Sep. 23, 2010

Related U.S. Application Data

(60) Provisional application No. 61/161,501, filed on Mar. 19, 2009.

(51) Int. Cl.
C07C 5/333    (2006.01)

(52) U.S. Cl.
USPC ........... 585/659; 585/435; 585/440; 585/444; 585/441; 585/654; 585/660; 585/661

(58) Field of Classification Search
USPC ......... 585/435, 440, 444, 441, 654, 659, 660, 585/661
See application file for complete search history.

(56) References Cited

U.S. PATENT DOCUMENTS

| | | | |
|---|---|---|---|
| 2,921,102 A * | 1/1960 | Lowman | 585/602 |
| 2,982,798 A * | 5/1961 | Hachmuth et al. | 585/628 |
| 3,692,701 A | 9/1972 | Box, Jr. | |
| 3,888,762 A | 6/1975 | Gerhold | |
| 4,056,575 A | 11/1977 | Gregory et al. | |
| 4,056,576 A | 11/1977 | Gregory et al. | |
| 4,078,743 A * | 3/1978 | Kogan et al. | 502/230 |
| 4,080,394 A * | 3/1978 | Antos | 585/434 |
| 4,152,365 A | 5/1979 | Drehman | |
| 4,502,947 A | 3/1985 | Haddad et al. | |
| 4,595,673 A * | 6/1986 | Imai et al. | 502/227 |
| 4,746,643 A | 5/1988 | Buonomo et al. | |

(Continued)

FOREIGN PATENT DOCUMENTS

| | | |
|---|---|---|
| CN | 201140065 Y | 10/2008 |
| EP | 1074299 | 2/2001 |

(Continued)

OTHER PUBLICATIONS

Lide, CRC Handbook of Chemistry and Physics, 91st Ed., 2011 Internet Version.*

(Continued)

*Primary Examiner* — In Suk Bullock
*Assistant Examiner* — Bradley Etherton (57) ABSTRACT

A supported catalyst and process for dehydrogenating a hydrocarbon, the catalyst comprising a first component selected from the group consisting of tin, germanium, lead, indium, gallium, thallium, and compounds thereof; a second component selected from the group consisting of metals of Group 8 of the Periodic Table of the Elements and compounds thereof, and a support comprising alumina in the gamma crystalline form. The catalysts are especially active and efficient when employed in concurrent flow in a dehydrogenation reactor having an average contact time between the hydrocarbon and catalyst of from 0.5 to 10 seconds.

9 Claims, 5 Drawing Sheets

(56) References Cited

U.S. PATENT DOCUMENTS

| | | | |
|---|---|---|---|
| 4,786,625 A | 11/1988 | Imai et al. | |
| 4,902,849 A | 2/1990 | McKay et al. | |
| 4,914,075 A * | 4/1990 | Bricker et al. | 502/330 |
| 4,985,136 A | 1/1991 | Bartholic | |
| 5,019,353 A | 5/1991 | Harandi et al. | |
| 5,143,886 A | 9/1992 | Iezzi et al. | |
| 5,214,227 A | 5/1993 | Zhou et al. | |
| 5,219,816 A | 6/1993 | Zhou et al. | |
| 5,248,411 A | 9/1993 | Chan | |
| 5,254,788 A | 10/1993 | Gartside et al. | |
| 5,365,006 A | 11/1994 | Serrand | |
| 5,414,182 A | 5/1995 | Iezzi et al. | |
| 5,633,421 A | 5/1997 | Iezzi et al. | |
| 5,656,243 A | 8/1997 | Luckenbach et al. | |
| 6,031,143 A | 2/2000 | Buonomo et al. | |
| 6,362,385 B1 | 3/2002 | Iezzi et al. | |
| 6,756,340 B2 | 6/2004 | Voskoboynikov et al. | |
| 7,094,940 B2 | 8/2006 | Miracca et al. | |
| 7,102,050 B1 | 9/2006 | Lattner et al. | |
| 7,122,160 B2 | 10/2006 | Brookhart | |
| 7,185,741 B1 | 3/2007 | Rozenfeld | |
| 7,235,706 B2 | 6/2007 | Iezzi et al. | |
| 7,473,668 B2 | 1/2009 | Bartolini et al. | |
| 7,902,416 B2 | 3/2011 | Glover et al. | |
| 2002/0198428 A1 | 12/2002 | Iezzi et al. | |
| 2003/0028059 A1 | 2/2003 | Hamper et al. | |
| 2003/0196933 A1 | 10/2003 | Lomas et al. | |
| 2003/0232720 A1 * | 12/2003 | Alerasool et al. | 502/317 |
| 2004/0082824 A1 | 4/2004 | Lattner | |
| 2004/0092391 A1 | 5/2004 | Rokicki et al. | |
| 2004/0242945 A1 | 12/2004 | Pelati et al. | |
| 2004/0266612 A1 | 12/2004 | Hayes et al. | |
| 2005/0075243 A1 | 4/2005 | Fridman et al. | |
| 2005/0177016 A1 * | 8/2005 | Sanfilippo et al. | 585/444 |
| 2008/0194891 A1 | 8/2008 | Pretz et al. | |
| 2010/0168493 A1 | 7/2010 | Le Peltier et al. | |
| 2011/0230698 A1 | 9/2011 | Towler et al. | |

FOREIGN PATENT DOCUMENTS

| | | |
|---|---|---|
| GB | 1499297 | 1/1978 |
| WO | 02051543 | 7/2002 |
| WO | 03083014 | 10/2003 |

OTHER PUBLICATIONS

Hill et al., "Integrated Study of the Calcination Cycle from Gibbsite to Corundum", Chemistry of Materials (2007), 19 (11) 2877-2883, 2007, month unknown.

Antos et al., Catalytic Naphtha Reforming Science and Technology, Marcel Dekker, Inc., 1995, p. 82.

* cited by examiner

Fig. 5

DEHYDROGENATION PROCESS AND CATALYST

CROSS-REFERENCE TO RELATED APPLICATION(S)

This application claims benefit of priority from U.S. Provisional Patent Application No. 61/161,501, filed Mar. 19, 2009, which application is incorporated by reference herein in its entirety.

BACKGROUND OF THE INVENTION

This invention generally relates to certain novel supported catalysts used for the catalytic dehydrogenation of paraffinic hydrocarbons to olefinic hydrocarbons, and/or lower alkylaromatic hydrocarbons to vinyl aromatic hydrocarbons. In several preferred embodiments, the invention relates to the dehydrogenation of lower alkanes, for example ethane, isopropane, propane and butanes to their corresponding olefins, for example ethylene, propylene and butylenes; and/or to the dehydrogenation of lower alkylaromatic hydrocarbon compounds, for example ethylbenzene, propylbenzene and methylethylbenzene to their corresponding vinyl aromatic (that is "alkenyl-aromatic") hydrocarbon compounds, for example styrene, cumene and alpha-methyl styrene, respectively. The invention further includes an integrated process for making olefinic and vinyl aromatic hydrocarbons including alkylation and dehydrogenation steps.

DESCRIPTION OF RELATED ART

In WO2005/077867 (US-A-2008/0194891) a process for the dehydrogenation of hydrocarbons using a "riser" reactor is disclosed. Such reactors are adapted from the hydrocarbon refining industry and provide extremely short contact times between catalyst and feedstock. The process was suited for use for the dehydrogenation of a single aliphatic or alkylaromatic hydrocarbon, especially ethylbenzene, to prepare the corresponding unsaturated derivative, especially styrene, or in a process to prepare multiple products from mixtures of hydrocarbons, such as a process for simultaneously preparing ethylene and styrene from a mixture of ethane and ethylbenzene. The process could also be employed as part of an integrated process for producing styrene by feeding benzene and recycled ethylene to an alkylation reactor to produce ethylbenzene, mixing the alkylation effluent with ethane and feeding the mixture to a dehydrogenation reactor containing a catalyst capable of contemporaneously dehydrogenating ethane and ethylbenzene, and then separating the resulting products to produce a stream of styrene and ethylene, with ethylene being recycled to the alkylation reactor.

Advantageously, the foregoing process minimized the time period in which reactants and catalyst are in contact with one another while at reaction temperature, resulting in extremely high selectivity to the desired products. Despite the advance brought by the foregoing process, improved product conversion while maintaining the high selectivities of the foregoing processes is a long desired yet, until now, unattained goal.

Suitable catalysts for use in the foregoing processes include those disclosed in WO 2002/096844, (U.S. Pat. No. 6,031,143, EP 0 905 112), which are based on gallium and platinum supported on alumina in the delta or theta phase, or in a mixture of delta plus theta phases, or theta plus alpha phases, or delta plus theta plus alpha phases, modified with silica, and having a surface area preferably less than 100 m²/g. More particularly, the foregoing catalysts comprise:

i) from 0.1 to 34 percent by weight, preferably 0.2 to 3.8 percent by weight of gallium oxide ($Ga_2O_3$);
ii) from 1 to 200 parts per million (ppm), preferably 100 to 150 ppm by weight of platinum;
iii) from 0.05 to 5 percent be weight, preferably 0.1 to 1 percent by weight of an alkali metal and/or alkaline earth metal such as potassium;
iv) from 0.08 to 3 percent by weight silica;
v) the balance being alumina in the foregoing delta or theta and optionally alpha phases. Similar gallium and platinum based catalyst are described in WO 2003/053567 which further includes manganese; US 2004/02242945 which further includes zinc, and in EP-B1-0,637,578. WO93/12879 disclosed supported catalysts for the dehydrogenation of light paraffins comprising Ga and Pt incorporated into a magnesium aluminate spinel having the formula $Mg_xAl_2O_{3+x}$, where x is a number from about 0.1 to 1.1. Such aluminate spinels are preferentially prepared from aluminas that upon calcination form gamma alumina. Other dehydrogenation catalysts based on metal aluminate spinels are disclosed in U.S. Pat. Nos. 4,902,849, 4,152,365 and 3,692,701.

Processes utilizing a riser reactor in dehydrogenation reactions in addition to the foregoing WO2005/077867, include WO 02/096844 which uses a split "riser-type" dehydrogenation reactor operating in concurrent or "equicurrent" mode wherein catalyst is carried upwards pneumatically through the dehydrogenation reactor by the gas phase reactants. The space velocity (GHSV) for such a reactor is greater than 500 $h^{-1}$. The catalyst is introduced into the reactor with an alkane such as ethane whereas the alkylaromatic compound, for example ethylbenzene, is introduced at a suitable height along the riser after much of the alkane has been dehydrogenated and the temperature of the catalyst has been reduced.

Integrated processes for producing unsaturated hydrocarbons from mixtures of reagents employing conventional reactors are further disclosed in WO 2003/053567, WO 02/096844, and EP 1 255 719 (US 2003/0028059), among other references.

SUMMARY OF THE INVENTION

According to the present invention there is now provided a novel supported catalyst for use in the dehydrogenation of hydrocarbons comprising:
i) a first component selected from the group consisting of tin, germanium, lead, indium, gallium, thallium, and compounds thereof;
ii) a second component selected from the group consisting of the metals of Group 8 of the Periodic Table of the Elements and compounds thereof,
ii) from 0.0 to 2.0 percent of an alkali metal or alkaline earth metal or compound thereof, and
iv) a support comprising alumina in the gamma crystalline form.

In a preferred embodiment, the foregoing catalyst comprises
i) from 0.25 to 5.0 percent, preferably 0.3 to 3.0 percent of the first component, preferably gallium, or a compound thereof;
ii) from 0.0005 to 0.05 percent, preferably 0.0007 to 0.04 percent of the second component, preferably platinum, or a compound thereof;
iii) from 0.0 to 2.0 percent, preferably 0.1 to 1.0 percent of an alkali metal or alkaline earth metal; and
iv) a support comprising alumina in the gamma crystalline form.

It will be understood by the skilled artisan that in the foregoing embodiments, the sum of the various components constitutes 100 percent. In a preferred embodiment the alumina support in the invented catalysts has a surface area greater than 90 m$^2$/g, more preferably greater than 100 m$^2$/g, and most preferably the surface area of the support is from 115 to 250 m$^2$/g.

The preparation of gamma alumina supports suitable for use herein may be accomplished by any known technique. A preferred technique involves heating of aluminum hydroxides or mixtures of aluminum hydroxides and oxides, especially pseudo-bohemite or microcrystalline bohemite to a temperature from about 300 to 800 degrees centigrade for a time sufficient to result in a clear transition of the crystalline structure to the disordered spinel gamma alumina phase. Highly desirably, the bohemite is a small particle size microspheroidal form prepared by spray-drying an aluminum hydroxide sol and the heating is conducted in the presence of air to a temperature from 500 to 750 degrees centigrade. This gamma alumina phase product is characterized by a relatively high surface area, suitable for use as a support herein.

In addition, the present invention provides an improved process for dehydrogenating a hydrocarbon comprising contacting a gaseous stream comprising at least one dehydrogenateable hydrocarbon with a supported dehydrogenation catalyst comprising a first component selected from the group consisting of tin, germanium, lead, indium, gallium, thallium, and compounds thereof; and a second component comprising a metal of Group 8 of the Periodic Table of the Elements or a compound thereof, at an elevated reaction temperature wherein the hydrocarbon and catalyst are in concurrent flow through a dehydrogenation reactor having an average contact time between the hydrocarbon and catalyst within the dehydrogenation reactor of from 0.5 to 10 seconds, said process further characterized in that the catalyst support comprises alumina in the gamma crystalline form. The foregoing process desirably employs a riser type reactor to achieve the extremely short contact times required of the process. Preferred catalyst supports comprise alumina in the gamma crystalline form having a surface area greater than 90 m$^2$/g, preferably greater than 100 m$^2$/g, and more preferably from 115 to 250 m$^2$/g. Highly desirably the catalysts used in the forgoing process are the previously disclosed supported dehydrogenation catalysts.

It has been discovered by the present inventors that operation of a dehydrogenation process according to the foregoing conditions and/or employing the foregoing catalysts beneficially allows the attainment of improved conversions of hydrocarbon reagents while at the same time achieving relatively high selectivities to the desired olefinically unsaturated reaction products. When reactors such as the foregoing riser type, including split-feed riser reactors are employed, highly desirable conversion products are readily and economically attainable. In addition, the cost to manufacture the present catalysts is significantly reduced compared to catalysts containing alumina supports in other crystalline forms, specifically delta, theta or alpha phases, because no calcination at temperatures greater than 800 degrees centigrade is employed during the manufacture of the present catalysts.

In general, the subject invention comprises contacting a gaseous stream of hydrocarbon with the previously disclosed dehydrogenation catalysts at reaction temperature for relatively short "contact times". In a preferred embodiment, lower alkanes, for example ethane, propane and butanes are dehydrogenated to their corresponding olefins, for example ethylene, propylene and butylenes; and/or lower alkylaromatic hydrocarbon compounds, for example ethylbenzene, propylbenzene and methylethylbenzene are dehydrogenated to their corresponding vinyl aromatic hydrocarbon compounds, for example styrene, cumene and alpha-methyl styrene, respectively.

In another embodiment, the aforementioned dehydrogenation process is combined with an alkylation step, as part of an integrated process. Many additional embodiments are also described.

DETAILED DESCRIPTION OF THE INVENTION

The term "aliphatic compound" as used herein refers to hydrocarbon compounds, a portion of which is capable of dehydrogenation to yield an aliphatically unsaturated compound. The term "substituted aliphatic compound" refers to an aliphatic hydrocarbon compound that contains one or more non-aliphatic hydrocarbon substituents and/or one or more non-hydrocarbon substituents with the proviso that the substituent or substituents do not prevent dehydrogenation of some remaining aliphatic portion of the compound. All reference to the Periodic Table of the Elements herein shall refer to the Periodic Table of the Elements, published and copyrighted by CRC Press, Inc., 2007. Also, any reference to a Group or Groups shall be to the Group or Groups as reflected in this Periodic Table of the Elements using the IUPAC system for numbering groups. For purposes of United States patent practice, the contents of any patent, patent application or publication referenced herein is hereby incorporated by reference in its entirety herein, especially with respect to its disclosure of processes, synthetic techniques and general knowledge in the art.

If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise, refers to the listed members individually as well as in any combination. Parts, including parts-per-million (ppm), and percentages herein are based on weight. Surface areas herein are determined by BET method, known to those of skill in the art.

The present invention is directed toward the dehydrogenation of at least one and preferably both of: 1) one or more paraffinic hydrocarbon compounds, preferably lower alkanes having from 2 to 6 carbon atoms but more preferably less than 5 carbon atoms, for example ethane, propane, isopropane and butanes, to the corresponding olefin, namely, ethylene, propylene, and butylenes, respectively, and 2) an alkylaromatic hydrocarbon compound, preferably a lower alkylaromatic hydrocarbon compound, such as for example, ethylbenzene, propylbenzene, isopropyl benzene, or methyl ethylbenzene, to the corresponding vinyl aromatic hydrocarbon compound, (that is "alkenylaromatic"), namely, styrene, cumene or alpha-methyl styrene. Several embodiments of the present invention are described including both the simultaneous and separate dehydrogenation of lower alkanes and alkylaromatics. The invention is useful to prepare styrene and ethylene from ethylbenzene and ethane, respectively. Likewise, cumene and propylene can be prepared from propylbenzene and propane, respectively.

Preferred catalysts for use in the present invention are very active and are capable of dehydrogenating paraffin and alkylaromatic hydrocarbons in less than a few seconds at ideal reaction temperatures. Highly desirably, the atomic ratio of first component (tin, germanium, lead, indium, gallium, thallium or compounds thereof) to Group 8 metal (Fe, Ru, Os, Co, Rh, Ir, Ni, Pd, or Pt) lies within the range from 0.1 to 1000, preferably from 1 to 500, and most preferably from 1 to 200. The alkali metal or alkaline earth metal compound is present in an amount to provide from 0.0 to 2.0 percent, preferably 0.1 to 1.0 percent metal, preferably alkali metal, most preferably K, in the resulting catalyst. It is to be understood by the skilled artisan that other components besides the foregoing first and second components, alkali metal or alkaline earth metal, and support, are substantially or wholly absent. In a preferred embodiment, there in no detectable quantity of any non-recited component, especially manganese or zinc.

The catalysts can be used as such or diluted with an inert material, for example, refractory oxides and other ceramics, such as metal- or metalloid-carbides, oxides or nitrides. Examples include silicon carbide and alumina having surface area of 50 $m^2/g$ or less. The inert additive may be used at a concentration of the inert product of between 0 and 50 percent, preferably from 5 to 25 percent of the total catalyst.

Details on the preparation of catalysts suitable for use herein are analogous to those employed in WO2005/077867 (US-A-2008/0194891), WO 2002/096844, (U.S. Pat. No. 6,031,143, EP 0 905 112), U.S. Pat. No. 6,031,143 and EP-B1-0,637,578. Typically, the process of preparing the aforementioned dehydrogenation catalysts comprises dispersing precursors of the catalytic metals, for example, solutions of soluble salts of the catalytic metals onto the preformed support. Suitable soluble salts particularly include the nitrate salts of the first component, especially gallium nitrate, and complexes of the Group 8 metal, such as tetraamineplatinum. More particularly, the foregoing process of dispersion can comprise impregnation of the carrier with one or more solutions containing the precursors of the first and second components, especially gallium and platinum, along with any other components, followed by drying and calcination. An alternative method comprises ion adsorption followed by the separation of the liquid portion of the adsorption solution, drying, and activation of the resultant solid. As another alternative, the carrier can be treated with volatile species of the desired metals. In the case of added alkali metals or alkaline earth metals, such compounds or their precursors may be added to the carrier prior to dispersion of the primary catalytic metals or compounds, followed, optionally, by calcination of the resulting solid. It will be understood by the skilled artisan that the actual species of each of the foregoing named components, under the conditions of their use as catalysts, may exist in the form of a compound, such as an oxide, and the metal or other component may be in an oxidation state other than that originally employed or designated herein. In its final active form, the preferred first component, gallium, is believed to be in the form of gallium oxide ($Ga_2O_3$). The alkali metal or alkaline earth metal, if present, is also believed to be in the form of an oxide.

The supports are prepared by previously disclosed techniques such as dehydration of soluble aluminum salts, especially aluminum hydroxides or mixtures thereof with aluminum oxides, and optionally silicates, followed by heating in the presence of air to a temperature from 300 to 800 degrees centigrade for time periods up to 24 hours. Additional compounds may optionally be present in the formulation in order to improve one or more physical properties of the support such as to increase abrasion resistance or decrease surface acidity. A preferred additive for this purpose is silica. When silica is employed in the support, it is preferably incorporated into the finished support by physically compounding with the previously prepared alumina. Preferred levels of silica incorporation are from 0.0 to 5.0 percent, more preferably 0.0 to 2.0 percent. In a highly preferred embodiment, microspheroidal pseudo-bohemite is prepared by spray drying a hydrated alumina sol to form particles suitably having an average particle size from 5 to 500 micrometers. This product is then heated to a temperature up to 800 degrees centigrade for a time up to about 8 hours. The drying may be accomplished in multiple steps at various temperatures to prevent loss of surface area. For example, the particles may be air dried at 350 degrees centigrade for 2 hours followed by heating at a temperature from 500 to 800, preferably 550 to 700 degrees centigrade for up to 4 hours. As is well known in the art, heating pseudobohemite to temperatures less than or equal to 800 degrees results in formation of the gamma alumina with substantially no formation of low surface area delta, theta or alpha crystalline phases, see, George J. Antos, et. al, ed., *Catalytic Naphtha Reforming Science and Technology*, Marcel Dekker, Inc., pg 82, and M. Hill, et al., *Chemistry of Materials* (2007), 19(11) 2877-2883. Highly preferably, the alumina in the supports used in the present invention primarily comprises the gamma crystalline form, more preferably still it consist essentially of gamma alumina, and highly desirably it consists or consists substantially entirely of gamma alumina.

As mentioned, the catalysts for use with the present invention are very active and are capable of completing the dehydrogenation reaction in a relatively short reaction time, for example in a matter of seconds. The use of the present catalysts and process conditions can result in the production of dehydrogenation products in selectivities greater than 99.0 percent, preferably greater than 99.5 percent and conversions of at least 60 percent, preferably at least 65 percent, and as high as 70 percent, or more. The use of relatively short catalyst contact times also decreases the amount of catalyst required for the process, resulting in lower catalyst inventory and operating costs compared with prior art processes. Finally, because the catalyst support comprises gamma alumina having high surface area, the process of calcining alumina at high temperatures (greater than 800 degrees centigrade) to alter the crystal structure is avoided, thereby further simplifying and reducing the cost of catalyst preparation.

The dehydrogenation reaction in the present invention is conducted under a relatively short contact times in order to prevent undesirable side reactions and product degradation. The term "average contact time" or "contact time" as used herein is intended to refer to the time in which the molar average of gaseous hydrocarbon molecules are in contact with catalyst while at reaction temperature, regardless of whether the reactants are converted to desired products. The term "reaction temperature" is intended to mean a temperature at which a significant amount of chemical reaction occurs, regardless of whether such reactions are the desired dehydrogenation of reactants to their corresponding olefin and vinyl aromatic products. Said another way, the reaction temperature is the temperature at which the hydrocarbons are no longer stable. The term "significant amount" in intended to mean a detectable amount having in an economic impact on the process. In most embodiments of the invention, the reaction temperature is greater than 500 degrees centigrade and preferably greater than 550 degrees centigrade. The average contact time needs to be sufficiently long to dehydrogenate acceptable amounts of hydrocarbon reactants but not so long as to result in unacceptable amounts of by-products. While the required contact time is related to the specific reactants, catalysts and reaction temperatures, in preferred embodiments of the invention the contact time within the dehydrogenation reactor is less than 60 seconds, preferably from 0.5 to 10 seconds, more preferably from 1 to 8 seconds, and still more preferably from 1 to 4 seconds.

Due to the active nature of the present catalysts, the average residence time of the catalyst within the dehydrogenation reactor is preferably less than 60 seconds, more preferably from 0.5 to 40 seconds, more preferably 1.0 to 20.0 seconds, and still more preferably from 5.0 to 15.0 seconds.

At such short catalyst residence times and average contact times in the dehydrogenation reactor, the temperature of the reaction mixture, which may be supplied in major part by the hot fresh or regenerated catalyst, is preferably from 500 to 800 degrees centigrade. With respect to lower alkanes, the reaction mixture is preferably from 600 to 750 degrees centigrade, and with respect to alkylaromatics from 550 to 700 degrees centigrade, but more preferably from 570 to 660 degrees centigrade. In general, the highest temperature in the reactor will be found at its beginning (lower end) and as reaction proceeds and the catalyst and reaction mixture ascends or rises in the reactor, the temperature will decrease toward the exit at the upper end of the reactor.

The applicable operating pressure of the dehydrogenation reactor is quite broad, that is from 3.7 to 64.7 psia (0.3-4.5 Kg/cm$^2$). In some applications, the pressure at which the reaction proceeds is elevated above atmospheric pressure, typically from 14.7 to 64.7 psia (1.0-4.5 Kg/cm$^2$), and preferably from 14.7 to 44.7 psia (1.0-3.1 Kg/cm$^2$). However, in several preferred embodiments of the invention, the operating pressure of the dehydrogenation reactor may be below atmospheric, that is from 3.7 to 14.7 psia (0.3-1.0 Kg/cm$^2$), more preferably 6.0 to 14.7 psia (0.4-1.0 Kg/cm$^2$).

The gas hourly space velocity (GHSV) for the present process has been found to range from 1,000 to 150,000 normal cubic meters/hr of hydrocarbon feed per cubic meter of catalyst at bulk density. The superficial gas velocity of 5.0 to 80.0 ft/sec (1.5-24.4 m/sec), preferably 15.0 to 70.0 ft/sec (4.6-21.3 m/sec). The catalyst flux is preferably 10.0 to 120 lbs/ft$^2$-sec (48.8-586 Kg/m$^2$-sec) with a catalyst to feed ratio of 5 to 100 on a weight to weight basis. The catalyst is preferably pneumatically moved through the reaction system by a carrier fluid, which is preferably either an inert diluent fluid or one of the reactants in gaseous form. Alternatively, the catalyst may be transported through the reactor under sub atmospheric pressure without diluent. Examples of inert diluent carrier gases are nitrogen, volatile hydrocarbons for example methane, and other carriers which do not interfere with the reaction, steam, carbon dioxide, argon and the like. The paraffinic hydrocarbon compounds useful as reactants in the process of the present invention are also preferred carrier fluids and, most preferred are ethane, propane, and butane. Steam is preferably not used in the present invention. The amount of carrier gas required is only that amount necessary to maintain the catalyst particles in fluidized state and transport the catalyst from the regenerator to the reactor. Preferably, the amount of carrier gas employed can range from 0 to 0.2 kg gas/kg catalyst. Injection points for carrier gas, especially reactant feed material carrier gas can be made at multiple points along the fresh or regenerated catalyst transfer line connecting the regenerator with the lower end of the riser reactor. The carrier gas will exit the reactor with the product gas or through the vent stream of the regenerator. In the case where the carrier gas is also a reactant, a considerable portion of the carrier gas may be reacted and leave with the product gas stream from the reactor.

The short contact time required by the present invention can be accomplished by way of a number of known reactor designs including fast fluidized, riser and downer reactors. Suitable riser reactors are disclosed in WO2005/077867 (US-A-2008/0194891. Additional riser reactor designs are commonly employed in conversion of certain petroleum fractions into gasoline in fluidized bed catalytic cracking (FCC) processes. See for example U.S. Pat. No. 3,888,762 which describes a short-time dilute-phase riser reactor designed for contact times of 10 seconds, and which further includes catalyst regeneration and recycle. See also: US Publication No. 2004/0082824; WO 2001/85872 and WO 2004/029178. Preferred reactors for use herein are riser reactors or split riser reactors.

In a preferred embodiment of the present invention the alkylaromatic hydrocarbon compound and/or the paraffinic hydrocarbon compound are introduced to the lower end of a reactor and contacted by the hot fresh or regenerated catalyst which is pneumatically moved by a carrier gas. As the hydrocarbon compound(s) rise in the cylindrical reactor with the catalyst, the dehydrogenation reaction takes place and at the top or upper end of the riser, the vinyl aromatic hydrocarbon compound and/or lower olefin is separated from the catalyst. The riser reactor can be constructed from conventional materials used in FCC or petrochemical processing and is conveniently a steel vessel using an alloy sufficient for containing the hydrocarbon materials of the reaction, considering the temperature, pressure and flow rates employed and may be refractory lined. The dimensions of the riser reactor are dependent on the process design of a processing facility, including the proposed capacity or throughput, gas hourly space velocity (GHSV), temperature, pressure, catalyst efficiency and unit ratios of feed converted to products at a desired selectivity.

The separation of gaseous hydrocarbon and catalyst is conveniently accomplished by means of a centrifugal impingement separator, such as a cyclone separator, but the separation can by done by any conventional means for solid-gas separations, including filtration and liquid suspension. It is important to minimize the average contact time between the catalyst and hydrocarbon once they exit the dehydrogenation reactor. This is preferably accomplished by at least one of two means; physical separation of catalyst from hydrocarbon, and cooling the catalyst and/or hydrocarbon to a temperature below the reaction temperature of hydrocarbon present. The average contact time of the catalyst and hydrocarbon at reaction temperature in the separation device is typically less than 60 seconds, preferably less than 10 seconds, and more preferably less than 5 seconds, and still more preferably less than 3 seconds. The separation device may be a conventional solid-gas impingement separator, such as cyclone separators commonly used in FCC applications. Preferred cyclone separators include two staged or "coupled" designs including both positive and negative pressure designs. Further examples are provided in U.S. Pat. Nos. 4,502,947; 4,985,136 and 5,248, 411. Once separated, the catalyst is either recycled to the dehydrogenation reactor or transferred to a regenerator.

In addition to separating the catalyst and hydrocarbon, the separation device may include a heat exchanger and/or quenching unit for delivering a fluid to cool the catalyst and/or hydrocarbons to a temperature below the reaction temperature. Such fluid may be delivered via a conventional quenching design including pressurized nozzles for delivering quenching fluid, for example liquid styrene, water, and the like. Such quenching technology is available from Stone & Webster and BP Amoco.

The average contact time between the catalysts and hydrocarbons while at reaction temperature through the entire dehydrogenation reactor and separation device is preferably less than 60 seconds more preferably less than 20 seconds, and still more preferably less than 10 seconds, and event more preferably less than 7 seconds.

Once separated, the gaseous hydrocarbon is further separated, that is aromatics and non-aromatics, which may be part of an integrated process as described in U.S. Pat. No. 6,031, 143; WO 02/096844; and US 2003/0028059. The spent catalyst may then optionally be sent to a stripper, and then either to a regenerator or recycle loop, after which the catalyst is returned to the dehydrogenation reactor. During regeneration the catalyst is contacted with a regeneration fluid, usually an oxygen-containing gas and optionally a fuel source such as methane or natural gas where remaining hydrocarbons, coke, heavy residues, and tar are removed from the catalyst, and the resulting regenerated catalyst is cycled back to the dehydrogenation reactor. A portion of the spent catalyst may be cycled back to the dehydrogenation reactor without regeneration via a recycle loop. Recycled spent catalyst may be combined with regenerated catalyst as a means of controlling temperature and catalyst activity within the dehydrogenation reactor. The combination of recycled and regenerated catalyst may be optimized based upon feedback from the output of the dehydrogenation reactor. An example of a means for controlling this combination is described in WO 03/083014. Examples of both regeneration and recycle configurations are provided in U.S. Pat. No. 3,888,762 and US-A-2003/0196933.

Figure 1:
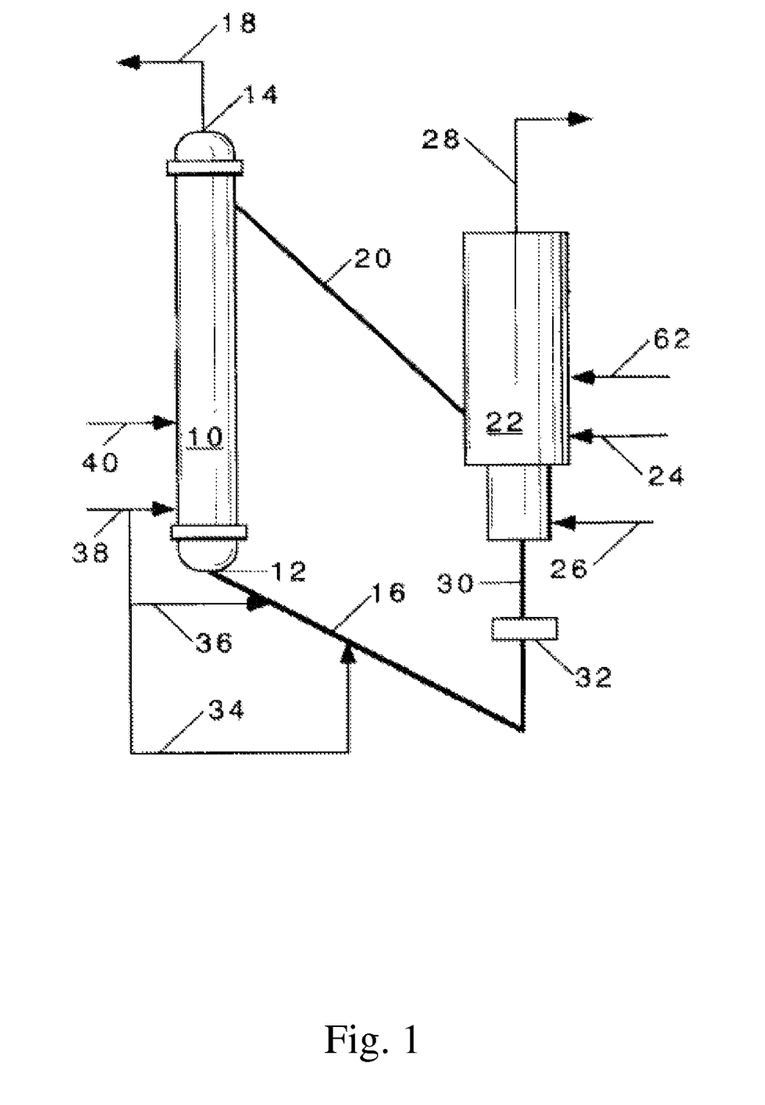
FIG. 1 shows a schematic block flow diagram of an embodiment of the present invention in which a riser reactor is employed in a single hydrocarbon feed point which may be used for: 1) paraffinic hydrocarbon (for example ethane) feed only, 2) alkylaromatic hydrocarbon (for example ethylbenzene) feed only, or 3) mixed feed (for example ethane and ethylbenzene), including catalyst regeneration.

Several preferred embodiments of the invention are illustrated in the attached figures. Turning to FIG. 1, a tubular cylindrical riser reactor 10 having a lower end 12 and an upper end 14 is connected at its lower end 12 to a fresh or regenerated catalyst transfer line 16 and at its upper end 14 to a product gas exit line 18. Spent or deactivated catalyst is removed from the product gas at upper end 14 by a separation device (not shown) which can be a conventional solid-gas impingement separator, such as a cyclone separator as previously described, and the catalyst is sent via spent catalyst transfer line 20 to regenerator 22 which is a reaction vessel in which combustion air is blown into the regenerator 22 by means of air line 24. Supplemental fuel may be added via fuel line 62 to provide the heat of reaction and necessary sensible heat, including the heat of vaporization in the case of liquid feed in the riser reactor 10. The combustion products from the oxidation of hydrocarbon on the catalyst are removed from the regenerator 22 by means of vent gas line 28. Prior to being sent for disposal or additional heat recovery, the vent gas may be filtered for removal of catalyst fines and dust by conventional equipment which is not shown. As a result of the combustion and hydrocarbon removal the catalyst is regenerated and heated to a temperature sufficient to dehydrogenate the hydrocarbon feed materials and is removed from the regenerator 22 by means of regenerated catalyst exit line 30. Fluidization is maintained by injection of a diluent or carrier gas, for example nitrogen, by means of nitrogen injection lines 26 and 32, and carrier gas injection lines 34, 36, and 38, so that catalyst is introduced to the lower end 12 of riser reactor 10 where it contacts ethane which is introduced via hydrocarbon feed line 40.

While FIG. 1 has been described with reference to the dehydrogenation of ethane, it will be appreciated that the present invention, along with the embodiment of FIG. 1 is also applicable for the dehydrogenation of other hydrocarbons, including lower alkanes such as propane and butane, and lower alkylaromatics, such as ethylbenzene, propylbenzene and methylethylbenzene.

In operation, the embodiment shown in FIG. 1 proceeds by feeding regenerated catalyst at a temperature of from 600 to 800 degrees centigrade from the regenerator 22 by means of regenerated catalyst exit line 30 into fresh or regenerated catalyst transfer line 16 with the catalyst being maintained in a fluid state of a Geldart A solid particulate material by means of fluidizing inert gas, such as nitrogen, fed through nitrogen injection lines 26 and 32, and carrier gas, which may be inert (again, such as nitrogen) or a reactant gas, such as a paraffinic hydrocarbon, such as for example, a lower alkane, preferably ethane, propane, or a butane, via carrier gas injection lines 34, 36, and 38. This catalyst and carrier gas mixture is introduced to the lower end 12 of riser reactor 10 and contacts a hydrocarbon feed in liquid or gaseous form, preferably the latter, introduced by means of hydrocarbon feed line 40. The catalyst and hydrocarbon feed, for example, a lower alkane, such as ethane, propane or a butane, or an alkylaromatic hydrocarbon compound, or a mixture of both lower alkane and an alkylaromatic hydrocarbon compound, contacts the catalyst and rises in the riser reactor 10 with the catalyst, feed (which by this time has been transformed into a gas) and the carrier gas. As the catalyst-feed-carrier gas mixture rises in the reactor, the dehydrogenation reaction occurs and the feed is converted into a lower olefin and/or a vinyl aromatic compound, depending on the feed material. As the reaction mixture containing gas and catalyst arrives at the upper end 14 of riser reactor 10, the catalyst and gaseous reaction mixture are separated by a solid-gas separation device, such as an impingement separation device which may preferably be a cyclone gas-solid separator, which is conventional and not shown, but which is well known to those of skill in the art of the FCC industry. The separated product gas is sent to recovery and purification and the catalyst is sent for regeneration and re-heating by means of spent or deactivated catalyst transfer line 20. As the spent or deactivated catalyst is introduced into the regenerator 22, it contacts heated combustion air which is introduced by air line 24 and supplemental fuel introduced by fuel line 62, such that the hydrocarbon materials remaining on the surface of the catalyst are burned off and exit the regenerator via vent gas line 28. The combustion process also serves a second purpose and that is to heat the catalyst so that the catalyst can function as a heat transfer agent or medium in the riser reactor 10. As used in this embodiment, the hydrocarbon feed 40 can be a paraffinic hydrocarbon such as a lower alkane, an alkylaromatic hydrocarbon compound, or a mixture of the two.

Figure 2:
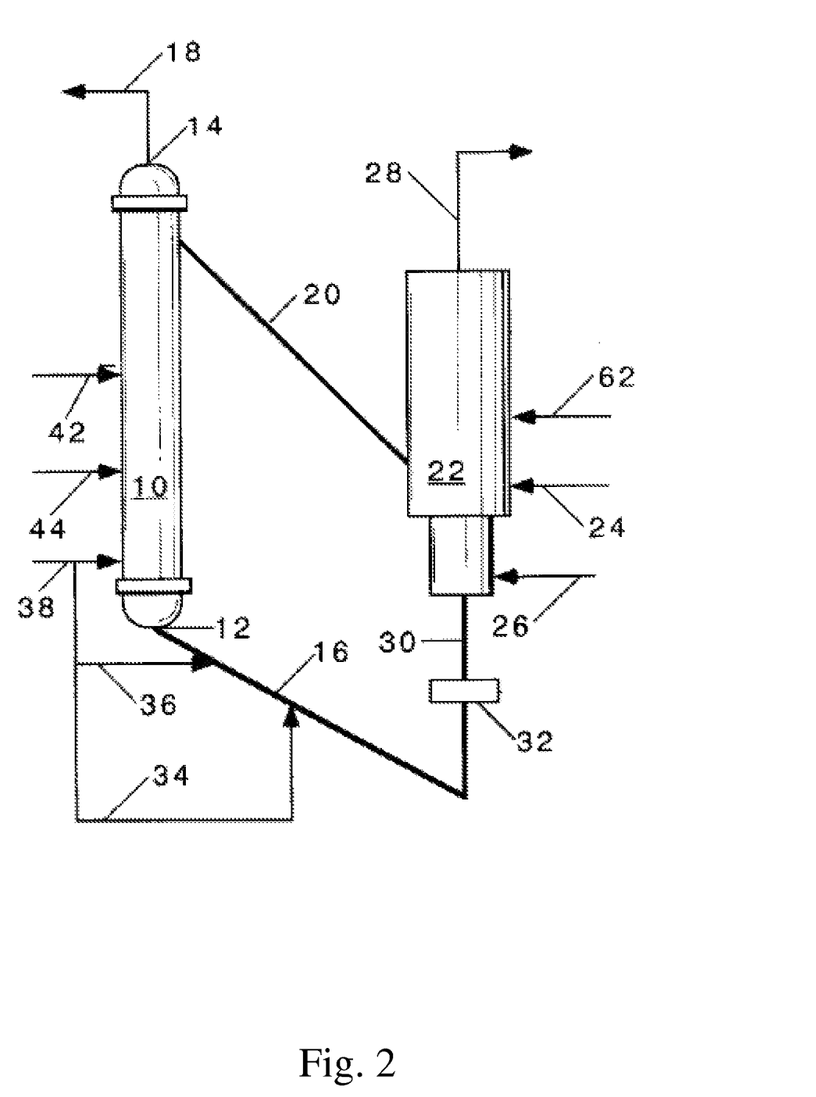
FIG. 2 shows a schematic block flow diagram of another embodiment of the present invention in which a riser reactor is employed with a multiple feed point configuration, that is a split ethylbenzene and ethane feed configuration, including catalyst regeneration.

FIG. 2 illustrates another preferred, non-limiting embodiment which is a variant on the process of the present invention using a similar riser reactor 10 configuration as described with respect to FIG. 1. In this embodiment the paraffinic hydrocarbon (for example ethane) is fed to the riser reactor 10 at or adjacent the lower end 12 by means of ethane feed line 44 and the lower alkylaromatic hydrocarbon compound (for example ethylbenzene), is fed at a higher point in the riser reactor 10, for example at ethylbenzene feed line 42. Thus, the type of reaction illustrated by the process of FIG. 2 is a "split feed" riser reactor process which produces styrene and by-products, such as ethylene which can be returned to an alkylation step to react with additional benzene to produce more ethylbenzene as part of an integrated process.

Figure 3:
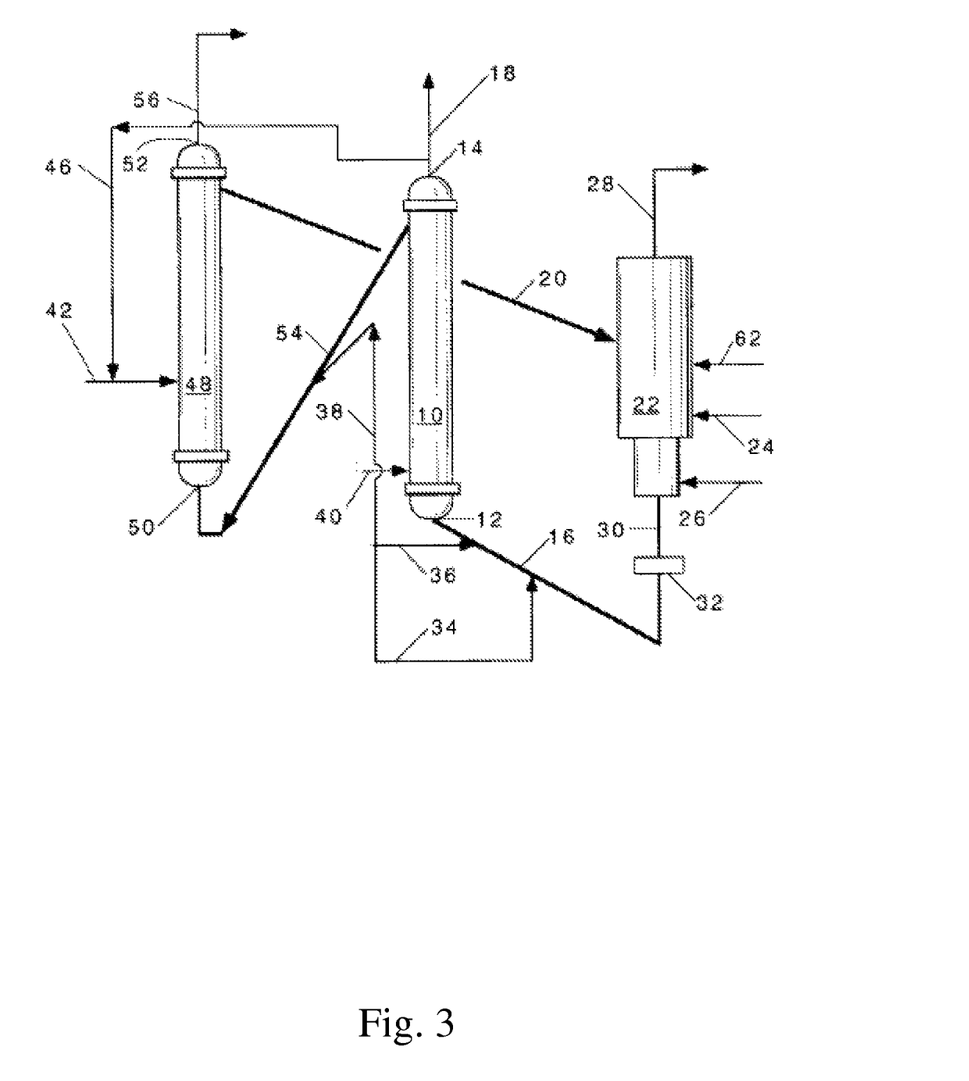
FIG. 3 shows a schematic block flow diagram of another embodiment of the present invention including multiple riser reactors with a catalyst regeneration in a series configuration.

FIG. 3 illustrates yet another preferred, non-limiting embodiment of the invention. In this embodiment, a "dual riser" reactor configuration is illustrated in which the riser reactors 10 and 48 are connected in series. As shown in FIG. 3, riser reactor 10 has lower end 12 and upper end 14. Connected to lower end 12 is fresh or regenerated catalyst line 16 and the catalyst is maintained in fluidized state by injection of carrier gas via lines 34 and 36. Hydrocarbon feed material, such as ethane, is introduced to the lower end 12 of riser reactor 10 by means of hydrocarbon feed line 40. At this stage of the process, the configuration is much like that of FIG. 1; however, the product gas from riser reactor 10 in FIG. 3 is fed to a separation and recovery section (not shown) by means of product gas exit line 18 from which a side product gas line 46 leads to an alkylaromatic hydrocarbon compound feed line, such as ethylbenzene feed line 42. Alternatively, both side product gas line 46, which carries primarily the lower olefin produced in riser reactor 10 in addition to by-products and carrier gas, can be fed separately into a second riser reactor, such as at 48, having a lower end 50 and an upper end 52. Also entering the lower end 50 of second riser reactor 48 is a partially deactivated catalyst line 54 which leads from the upper end 14 of riser reactor 10 to the lower end 50 of second riser reactor 48. Carrier gas line 38 can be used to introduce fluidizing carrier gas into partially deactivated catalyst line 54 at one or multiple points along partially deactivated catalyst line 54. As the ethylene and ethylbenzene rise in second riser reactor 48 with the catalyst and carrier gas, the catalyst is at a lower temperature than when initially introduced to the lower end 12 of riser reactor 10. The relatively lower temperature than in riser reactor 10 permits satisfactory reaction rates for the alkylaromatic hydrocarbon compound and prevents over reaction to undesired by-products, thus decreasing the yield, conversion and selectivity of the dehydrogenation reaction. The upper end 52 of second riser reactor 48 is connected to second product gas exit line 56 and can lead the vinyl aromatic hydrocarbon compound, such as crude styrene monomer contained in the product gases, into the product gas separation and recovery section, which is conventional and not further described or identified herein. Prior to exit from second riser reactor 48, the reaction mixture must be separated from the deactivated catalyst and this is done in a solid-gas separation device, such as a cyclone separator, not shown. The separated and deactivated catalyst is fed back to the regenerator 22 by means of spent or deactivated catalyst transfer line 20 which in this embodiment leads from the upper end 52 of second riser reactor 48 to the regenerator 22 where the catalyst is regenerated, as previously described. In operation, the process is much like that described in relation to the process illustrated in FIGS. 1 and 2, except that the product gas from the upper end 14 of riser reactor 10 is split and a portion is introduced into the lower end 50 of second riser reactor 48. Ethylbenzene is also introduced into the lower end 50 of second riser reactor 48 along with the partially deactivated catalyst via partially deactivated catalyst line 54 and the dehydrogenation of the ethylbenzene proceeds at somewhat milder conditions in second riser reactor 48 than in riser reactor 10. At the upper end 52 of second riser reactor 48, the product gases are separated from the catalyst in a solid gas separator device, such as a cyclone separator (which is conventional and not shown) and the product gases exit via second product gas exit line 56 and the catalyst is sent back to regenerator 22 for regeneration and reheating via spent or deactivated catalyst transfer line 20.

Figure 4:
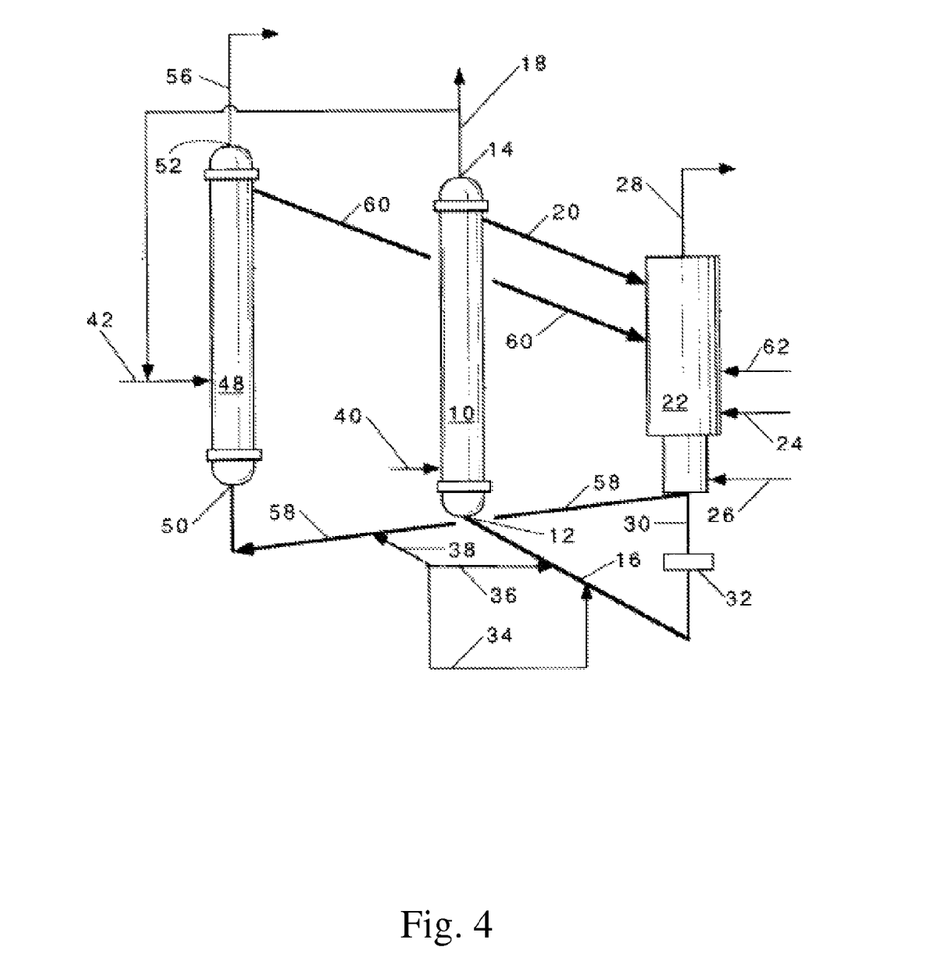
FIG. 4 shows a schematic block flow diagram of another embodiment of the present invention including multiple riser reactors with catalyst regeneration in a parallel configuration.

In a still further preferred embodiment of this invention shown in FIG. 4, the reactor/regenerator configuration is similar to that of FIG. 3, except that the second riser reactor 48 has its own catalyst feed and removal transfer lines, namely second fresh or regenerated catalyst transfer line 58 and second spent or deactivated catalyst transfer line 60 which feed active catalyst to second riser reactor 48 and remove catalyst from it and send the deactivated or spent catalyst back to regenerator 22. While shown as utilizing a common regenerator 22, it will be appreciated that each reactor may include a separate regenerator.

In operation and as shown in FIG. 4, the catalyst from regenerator 22 is led by regenerated catalyst exit line 30 to either riser reactor 10 or second riser reactor 48 via fresh or regenerated catalyst transfer line 16 or second fresh or regenerated catalyst transfer line 58, respectively. The feed to riser reactor 10 is ethane via hydrocarbon feed line 40 and to second riser reactor 48 is ethylbenzene via ethylbenzene feed line 42. On contact with the catalyst in the riser reactors, the ethane and ethylbenzene are converted into ethylene and styrene monomer, respectively, and the crude gaseous products are separated from the catalyst in gas-solid separators, such as cyclone separators (not shown) and sent to product gas separation and recovery operations (not shown) to produce ethylene for recycle to make additional ethylbenzene and styrene monomer, respectively. In a similar manner and using propane or butane instead of ethane feed, the process of this invention would dehydrogenate the feed to propylene or butylenes, respectively; or using isopropyl benzene or methyl ethyl benzene as feed material, the process of this invention would dehydrogenate the feed to cumene or alpha-methyl styrene, respectively.

Figure 5:
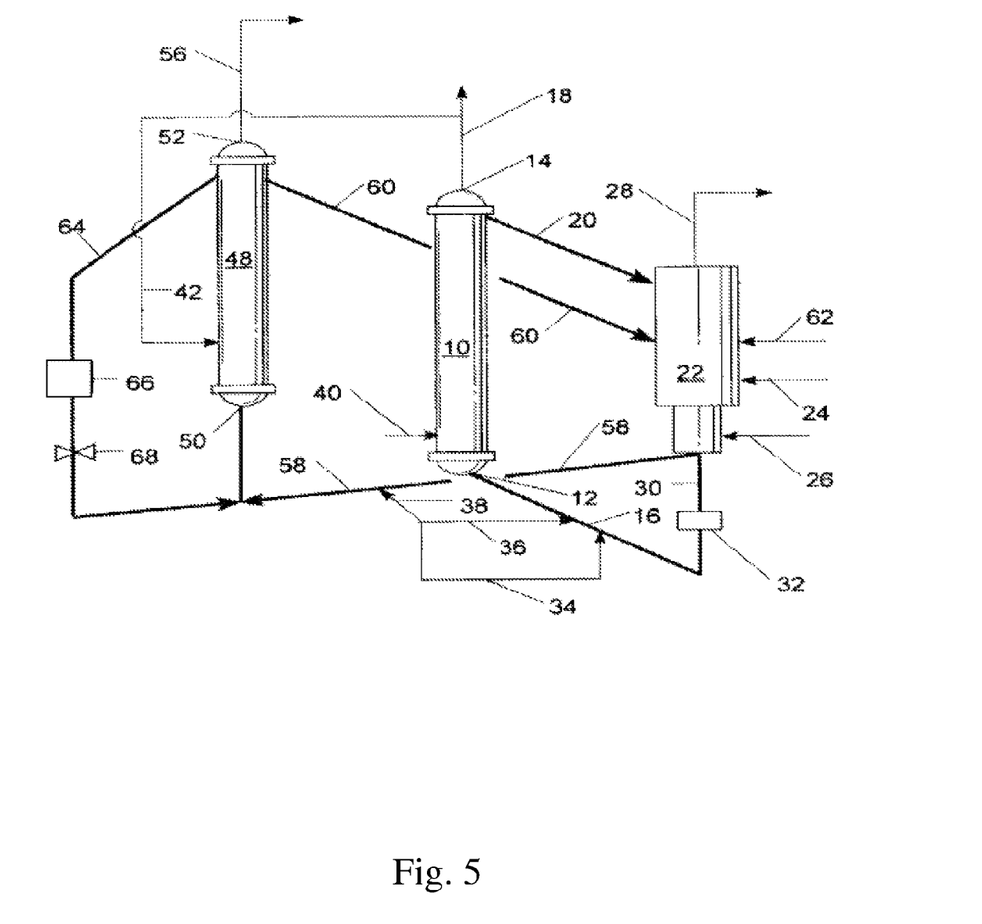
FIG. 5 shows a schematic block follow diagram of another embodiment of the present invention similar to FIG. 4, but further including a catalyst recycle configuration.

FIG. 5 illustrates yet another embodiment of the invention similar to that shown in FIG. 4 but with the addition of a catalyst recycle loop comprising a catalyst transfer line 64, carrier gas injector line 66 and flow valve 68. Spent catalyst is removed from the product gas at the upper end 52 of the dehydrogenation reactor 48 via a separation device (not shown) and is recycled back to the bottom end 50 of the reactor 48 via catalyst transfer line 64. Fluidization of the spent catalyst is maintained by the injection of a carrier gas, for example nitrogen by means of injection line in module 66. In addition to providing a carrier gas, an oxygen-containing gas may be introduced in order to partially reactivate the catalyst, in which case module 66 would include a chamber for reaction and removal of hydrocarbon residue. Flow of catalyst through the recycle loop is controlled by one or more valves, for example 68 which may be controlled remotely according to predetermined performance criteria including reactor 48 temperature, catalyst activity, or other parameter. Recycled catalyst may be combined with regenerated catalyst prior to introduction in the bottom of reactor 48, or may be introduced via separate entry points (not shown).

Additional configurations of the reactor(s), regenerator and recycle loop can be envisioned by one skilled in the art. For example, one skilled in the art will appreciate that multiple reactors could be arranged to feed into a common separation device with shared or separate catalyst regenerators and various recycle loops. The present invention is desired to be limited only by the lawful scope of the appended claims. The present invention does not preferably include oxidative dehydrogenation, that is oxodehydrogenation. In fact, oxygenates can poison the catalyst; however, oxygen may used to regenerate or reactivate catalyst during the regeneration process. Moreover, the present invention preferably does not utilize steam as is typically used in convention styrene production process.

Another preferred embodiment of the invention utilizes the previously described dehydrogenation process as part of an integrated process for making olefins and vinyl aromatics. More specifically, the previously described dehydrogenation, (along with regeneration and/or recycle processes) can be used to replace the dehydrogenation schemes described in WO2005/077867 (US-A-2008/0194891), U.S. Pat. No. 6,031,143; WO 02/096844; or US-A-2003/0028059. In such an integrated process, a paraffinic hydrocarbon such as a lower alkane, for example ethane, and benzene are the primary raw materials. Ethylene, preferably "recycled" and benzene are fed to a conventional alkylation reactor using a conventional catalyst such as aluminum chloride or zeolites. Variations include the use of dilute ethylene and a catalytic distillation approach where liquid phase alkylation and product separation take place simultaneously. Specific examples include the "EBOne Process" available from ABB Lummus/UOP, "EB Max Process" available from ExxonMobil/Badger and similar alkylation technology available from CDTECH, a partnership between ABB Lummus Global Inc. and Chemical Research and Licensing.

The alkylation affluent is recovered and optionally subject to separation, that is separation of aromatics from non-aromatics, removal of hydrogen, and other purification steps. Alkylaromatic compounds, for example ethylbenzene, and paraffinic hydrocarbons, for example ethane, are suitably simultaneously dehydrogenated using the present process. The gaseous products of dehydrogenation are recovered and separated, for example aromatics from non-aromatics, with vinyl aromatics, for example styrene being recovered, olefins, for example ethylene (and possibly paraffinic hydrocarbons, for example ethane) being recycled to the alkylation reactor, and alkylaromatics being recycled to the dehydrogenation reactor.

The present invention is hereby disclosed in greater detail according to the following preferred embodiments.

1. A process for dehydrogenating a hydrocarbon comprising contacting a gaseous stream comprising at least one dehydrogenatable hydrocarbon with a supported dehydrogenation catalyst comprising a first component selected from the group consisting of tin, germanium, lead, indium, gallium, thallium, and compounds thereof; and a second component selected from the group consisting of metals of Group 8 of the Periodic Table of the Elements and compounds thereof, at an elevated reaction temperature wherein the hydrocarbon and catalyst are in concurrent flow through a dehydrogenation reactor having an average contact time between the hydrocarbon and catalyst within the dehydrogenation reactor of from 0.5 to 10 seconds, said process further characterized in that the catalyst support comprises alumina in the gamma crystalline form, preferably having a surface area of at least 100 m$^2$/g, more preferably from 115 to 250 m$^2$/g.

2. The process of embodiment 1 wherein the catalyst has an average residence time within the dehydrogenation reactor from 0.5 to 40 seconds.

3. The process of embodiment 2 wherein the hydrocarbon and catalyst are transferred from the dehydrogenation reactor to a separation device wherein the average contact time between the hydrocarbon and catalyst while at reaction temperature in the separation device is less than 10 seconds.

4. The process of embodiment 3 wherein the total average contact time between the hydrocarbon, catalyst and resulting products while at reaction temperature is less than 20 seconds.

5. The process of embodiment 1 wherein the hydrocarbon is selected from paraffinic hydrocarbons having from 2 to 20 carbons, alkylaromatic hydrocarbons having from 8 to 20 carbons, and mixtures thereof.

6. The process of embodiment 5 wherein the paraffinic hydrocarbons are selected from ethane, propane, isopropane, and butane; and the alkylaromatic hydrocarbons are selected from ethylbenzene, propylbenzene and methylethylbenzene.

7. The process of embodiment 1 wherein the dehydrogenation reactor is a riser reactor.

8. The process of embodiment 1 wherein the hydrocarbon is introduced to the dehydrogenation reactor at multiple points of entry.

9. The process of embodiment 8 wherein both a paraffinic hydrocarbon and an alkylaromatic hydrocarbon are introduced into the same dehydrogenation reactor with the paraffinic hydrocarbon being introduced at a relatively lower point of entry than the alkylaromatic hydrocarbon, and products are removed at a point in the reactor that is higher in elevation than the entry points.

10. The process of embodiment 1 wherein the temperature within the dehydrogenation reactor is from 500 to 800 degrees centigrade and the pressure is from 3.7 to 64.7 psia (0.26 to 4.55 kg/cm$^2$).

11. The process of embodiment 10 wherein the pressure is from 5.0 to 14.7 psia (0.35 to 1.03 kg/cm$^2$).

12. The process of embodiment 10 wherein the temperature is from 570 to 750 degrees centigrade.

13. The process of embodiment 3 wherein catalyst from the separation device is transferred to a catalyst regenerator, wherein the catalyst is regenerated and returned to the dehydrogenation reactor, or a recycle loop wherein catalyst is recycled from the separation device back to the dehydrogenation reactor without regeneration.

14. The process of embodiment 13 wherein the catalyst from the recycle loop and regenerator are combined and reintroduced into the dehydrogenation reactor.

15. The process of embodiment 1 wherein the catalyst comprises:
  i) a first component selected from the group consisting of tin, germanium, lead, indium, gallium, thallium, and compounds thereof;
  ii) a second component selected from the group consisting of the metals of Group 8 of the Periodic Table of the Elements and compounds thereof,
  iii) from 0.0 to 2.0 percent of an alkali metal or alkaline earth metal or compound thereof, and
  iv) a support comprising alumina or silica modified alumina, said alumina being in the gamma crystalline form.

16. The process of embodiment 15 wherein the alumina or silica modified silica has a surface area from 115 to 250 m$^2$/g.

17. The process of embodiment 1 wherein the alumina consists essentially of alumina in the gamma crystalline form.

18. A process for dehydrogenating one or more hydrocarbons selected from the group consisting of paraffinic hydrocarbons and alkylaromatic hydrocarbons comprising contacting a gaseous stream containing at least one of the hydrocarbons with a supported dehydrogenation catalyst at reaction temperature and in concurrent flow through a dehydrogenation reactor wherein the average catalyst residence time within the dehydrogenation reactor from 0.5 to 40 seconds; the temperature in the dehydrogenation reactor is from 500 to 800 degrees centigrade, and the pressure in the dehydrogenation reactor is from 5.0 to 50 psia (0.35 to 3.5 kg/cm$^2$), characterized in that the supported dehydrogenation catalyst comprises a first component selected from the group consisting of tin, germanium, lead, indium, gallium, thallium, and compounds thereof; a second component selected from the group consisting of metals of Group 8 of the Periodic Table of the Elements and compounds thereof, and a support comprising alumina in the gamma crystalline form, preferably having a surface area of at least 100 m$^2$/g, more preferably from 115 to 250 m$^2$/g.

19. An integrated process for making a vinyl aromatic compound comprising dehydrogenating a paraffinic hydrocarbon and an alkylaromatic hydrocarbon with a supported dehydrogenation catalyst at reaction temperature and in concurrent flow through a dehydrogenation reactor wherein the average catalyst residence time within the dehydrogenation reactor from 0.5 to 40 seconds; the temperature in the dehydrogenation reactor is from 500 to 800 degrees centigrade, and the pressure in the dehydrogenation reactor is from 5.0 to 50 psia (0.35 to 3.5 kg/cm$^2$), characterized in that the supported dehydrogenation catalyst comprises a first component selected from the group consisting of tin, germanium, lead, indium, gallium, thallium, and compounds thereof; a second component selected from the group consisting of metals of Group 8 of the Periodic Table of the Elements and compounds thereof, and a support comprising alumina in the gamma crystalline form, preferably having a surface area of at least 100 m$^2$/g, more preferably from 115 to 250 m$^2$/g.

20. A process according to embodiment 21 wherein the dehydrogenation of the paraffinic hydrocarbon and alkylaromatic hydrocarbon is conducted concurrently in the same dehydrogenation reactor.

21. A supported catalyst for use in the dehydrogenation of hydrocarbons comprising:
i) a first component selected from the group consisting of tin, germanium, lead, indium, gallium, thallium, and compounds thereof;
ii) a second component selected from the group consisting of the metals of Group 8 of the Periodic Table of the Elements and compounds thereof,
ii) from 0.0 to 2.0 percent of an alkali metal or alkaline earth metal or compound thereof, and
iv) a support comprising alumina in the gamma crystalline form.

22. The catalyst according to embodiment 21 comprising
i) from 0.25 to 5.0 percent, preferably 0.3 to 3.0 percent of the first component, preferably gallium, or a compound thereof;
ii) from 0.0005 to 0.05 percent, preferably 0.0007 to 0.04 percent of the second component, preferably platinum, or a compound thereof;
iii) from 0.0 to 2.0 percent, preferably 0.1 to 1.0 percent of an alkali metal or alkaline earth metal, preferably potassium; and
iv) a support comprising alumina in the gamma crystalline form.

23. A supported catalyst according to embodiment 21 wherein the atomic ratio of gallium to platinum is from 0.1 to 1000.

24. A supported catalyst according to embodiment 21 wherein the support additionally comprises silica.

25. A supported catalyst according to embodiment 21 wherein the support consists essentially of gamma alumina.

26. A supported catalyst according to embodiment 24 wherein the alumina in the support consists essentially of gamma alumina.

EXAMPLES

Having described the invention the following examples are provided as further illustrative thereof and are not to be construed as limiting the invention.

Several supported catalysts are prepared using silica modified alumina samples having differing surface areas (Siralox™ alumina containing 1.5 percent SiO$_2$, available from SASOL Corporation). Support surface areas are measured using the BET method and have surface areas of 39, 70, 94 and 141 m$^2$/g, respectively. The supports are dried at 350 degrees centigrade for two hours. Potassium, gallium and Pt compounds are loaded by contacting the support samples with aqueous solutions of KNO$_3$, Ga(NO$_3$)$_3$ and tetraamine-platinum(II) nitrate until completely moistened (incipient wetness technique). The samples are then air dried at 23 degrees centigrade for 12 hours and at 120 degrees centigrade for 4 hours, followed by heating at 600 degrees centigrade in air for 4 hours. Final product composition is found to be 1.6 percent Ga, 0.25 percent K and 200 ppm Pt.

Catalyst evaluations are conducted in a fixed bed reactor. A mixture of 0.2 g of catalyst and 0.8 g of SiC is loaded to the reactor. Fresh catalysts are subjected to a conditioning period, in which ten reaction/regeneration cycles are conducted sequentially to establish a stable catalytic performance. In the process, a mixture of 15 mol percent ethylbenzene in ethane is dehydrogenated at 585 degrees C. for 10 minutes. The flow rate of ethane is 91 sccm and the feed rate of ethylbenzene is 4.6 g/h. After the dehydrogenation the reactor temperature is increased to 700 degrees centigrade under nitrogen. Catalyst regeneration is conducted at 700 degrees centigrade by introducing air into the reactor at a flow rate of 300 cm$^3$/minute for 15 minutes. After catalyst regeneration, the reactor is cooled to 585 degrees centigrade under nitrogen. After 10 such cycles the catalyst is ready for testing.

During testing, ethylbenzene in nitrogen is injected into the same reactor employed in the conditioning step for 30 seconds while maintaining the reactor at 600 degrees centigrade. The feed composition is 20 mole percent ethylbenzene in nitrogen with an ethylbenzene flow rate of 20.27 g/h giving a total gas hourly space velocity (GHSV) of 150,000 hr$_{-1}$. Ethylbenzene conversion and selectivity data are collected after 5 seconds time-on-stream. The ethylbenzene flow is then stopped and nitrogen at a flowrate of 300 sccm is continued for 15 minutes. The reactor temperature is then raised to 700 degrees centigrade under nitrogen flow of 300 sccm for 10 minutes. Catalyst regeneration follows by introducing air into the reactor for 15 minutes at a temperature of 700 degrees centigrade and a flow rate of 300 sccm. The reactor is then cooled to 600 degrees centigrade under a nitrogen flow of 300 sccm before again introducing ethylbenzene. The foregoing procedure is repeated for a total of 15 dehydrogenation/regeneration cycles. Average conversion and selectivity results are contained in Table 1. The results indicate that catalysts according to the invention, especially those with supports having surface areas of greater than 100 m$_2$/g and especially at least 140 m$_2$/g give the highest conversions, up to 70 percent, without loss of selectivity.

TABLE 1

| Run | Surface Area m²/g | conversion percent | selectivity percent |
|---|---|---|---|
| 1 | 39 | 30 | 99.5 |
| 2 | 70 | 49 | 99.7 |
| 3 | 94 | 59 | 99.3 |
| 4 | 141 | 70 | 99.5 |

What is claimed is:

1. A process for dehydrogenating a hydrocarbon comprising:
contacting a gaseous stream consisting essentially of:
(a) at least one dehydrogenatable hydrocarbon selected from paraffinic hydrocarbons having from 2 to 20 carbons, alkylaromatic hydrocarbons having from 8 to 20 carbons, and mixtures thereof, hydrogen produced in situ by the dehydrogenation and a carrier fluid selected from the group consisting of one of the reactants in gaseous form, nitrogen, volatile hydrocarbons, carbon dioxide, and argon; or
(b) at least one dehydrogenatable hydrocarbon selected from paraffinic hydrocarbons having from 2 to 20 carbons, alkylaromatic hydrocarbons having from 8 to 20 carbons, and mixtures thereof and hydrogen produced in situ by the dehydrogenation,
in a dehydrogenation riser reactor with a supported dehydrogenation catalyst comprising a first component selected from the group consisting of indium and gallium, and compounds thereof; a second component selected from the group consisting of the metals of Group 8 of the Periodic Table of the Elements and compounds thereof; from 0.0 to 2 percent of an alkali metal or alkaline earth metal or compound thereof; and a support comprising silica-modified alumina in the gamma crystalline form wherein the catalyst has an average residence time within the riser reactor from 0.5 to 40 seconds and catalyst to hydrocarbon ratio of 5 to 100 on a weight to weight basis;
transferring the hydrocarbon and catalyst from the dehydrogenation reactor to a separation device; and
transferring catalyst from the separation device to a regenerator where the catalyst is contacted with an oxygen-containing gas and supplemental fuel.

2. The process of claim 1 wherein the temperature within the dehydrogenation reactor is from 500 to 800 degrees centigrade and the pressure is from 3.7 to 64.7 psia (0.26 to 4.55 kg/cm²).

3. The process of claim 1 wherein the support has a surface area from 115 to 250 m²/g.

4. The process of claim 1 wherein the catalyst comprises:
i) from 0.25 to 5.0 percent gallium or a compound thereof;
ii) from 0.0005 to 0.05 percent platinum or a compound thereof; and
iii) from 0.0 to 2.0 percent of potassium.

5. The process of claim 4 wherein the support has a surface area from 115 to 250 m²/g.

6. The process of claim 1 wherein the atomic ratio of gallium to platinum is from 0.1 to 1000.

7. The process of claim 1 wherein the catalyst consists of only:
i) from 0.25 to 5.0 weight percent gallium or a compound thereof;
ii) from 0.0005 to 0.05 weight percent platinum or a compound thereof;
iii) from 0.0 to 2.0 weight percent of potassium or a compound thereof; and
iv) a support comprising alumina in the gamma crystalline form.

8. The process of claim 1 wherein the paraffinic hydrocarbons are selected from ethane, propane, isopropane, and butane; and the alkylaromatic hydrocarbons are selected from ethylbenzene, propylbenzene and methylethylbenzene.

9. An integrated process for dehydrogenating ethylbenzene and ethane comprising:
contacting a gaseous stream consisting essentially of a mixture of:
(a) ethane and ethyl benzene, hydrogen produced in situ by the dehydrogenation and a carrier fluid selected from the group consisting of one of the reactants in gaseous form, nitrogen, volatile hydrocarbons, carbon dioxide, and argon; or
(b) ethane and ethylbenzene and hydrogen produced in situ by the dehydrogenation;
with a supported dehydrogenation catalyst at reaction temperature and in concurrent flow through a dehydrogenation riser reactor wherein the average catalyst residence time within the dehydrogenation riser reactor from 0.5 to 40 seconds; the temperature in the dehydrogenation riser reactor is from 500 to 800 degrees centigrade, and the pressure in the dehydrogenation riser reactor is from 5.0 to 50 psia (0.35 to 3.5 kg/cm²), characterized in that the supported dehydrogenation catalyst consists of only:
i) 0.25 to 5.0 weight percent gallium or a compound thereof;
ii) 0.0005 to 0.05 weight percent platinum or a compound thereof;
iii) 0.0 to 2.0 weight percent of potassium or a compound thereof; and
iv) a support comprising silica-modified alumina in the gamma crystalline form;
transferring the hydrocarbon and catalyst from the dehydrogenation reactor to a separation device; and
transferring catalyst from the separation device to a regenerator where the catalyst is contacted with an oxygen-containing gas and supplemental fuel.

* * * * *